United States Patent [19]

Kishimoto et al.

[11] Patent Number: 5,126,325
[45] Date of Patent: Jun. 30, 1992

[54] METHOD FOR TREATING THROMBOCYTOPENIA

[75] Inventors: Tadamitsu Kishimoto, No. 5-31, Nakano 3-chome, Tondabayashi-shi, Osaka-fu; Toshio Hirano, Ibaraki; Hideo Kimura; Toshiyuki Ishibashi, both of Fukushima; Yukio Akiyama; Akira Okano, both of Kawasaki, all of Japan

[73] Assignees: Ajinomoto Co., Inc., Tokyo; Tadamitsu Kishimoto, Tondabayashi, both of Japan

[21] Appl. No.: 462,764

[22] Filed: Jan. 10, 1990

[30] Foreign Application Priority Data

Jan. 13, 1989 [JP] Japan .................................. 1-6954
Jun. 26, 1989 [JP] Japan .................................. 1-163087
Oct. 30, 1989 [JP] Japan .................................. 1-282297

[51] Int. Cl.⁵ .............................................. A61K 37/02
[52] U.S. Cl. .................................. 514/12; 424/85.1; 424/85.2
[58] Field of Search ................. 514/12; 424/85.1, 85.2

[56] References Cited

FOREIGN PATENT DOCUMENTS 8800206  1/1988  World Int. Prop. O. .

OTHER PUBLICATIONS

Van Damme et al., *Eur. J. Biochem.* 168:543-550 (1987).
Yasukawa et al., *EMBO J.* 6: 2939-2945 (1987).
Ishibashi et al., *Blood* 74(4) pp. 1241-1244 (1989).

*Primary Examiner*—David L. Lacey
*Assistant Examiner*—Shelly J. Guest
*Attorney, Agent, or Firm*—Oblon, Spivak, McClelland, Maier & Neustadt

[57] ABSTRACT

Thrombocytopenia is treated by administering to a subject a therapeutic amount of human B cell differentiation factor or its biological equivalent.

8 Claims, No Drawings

METHOD FOR TREATING THROMBOCYTOPENIA

BACKGROUND OF THE INVENTION

1. Field of the Invention

The present invention relates to the use of human B cell differentiation factor (abbreviated "h BCDF") for preparing compositions for treating thrombocytopenia (platelet deficiency).

More particularly, the present invention relates to the preparation of compositions for treating thrombocytopenia comprising human BCDF as the effective ingredient.

2. Description of the Background

Factors for differentiating mature B cells into antibody-producing cells in humans and mice are collectively called B cell differentiation factor (BCDF).

Human BCDF possesses activity which is important in the human body. Extensive research work in the recent past has led to the determination of the DNA sequence coding for BCDF and of the amino acid sequence of BCDF (Japanese Patent Application OPI Nos. 42688/88 and 56291/88). Further, human BCDF has been successfully produced using *E. coli* (Japanese Patent Application OPI No. 157996/88).

It has been found that human BCDF can be used as an immunotherapeutic agent which is effective in the treatment of infectious diseases and cancers (Japanese Patent Application No. 289007/87, OPI 63527/89).

The present inventors also found that human BCDF can be an effective supporting agent for bone marrow transplantation therapy (Japanese Patent Application No. 289007/87 and European patent application No. 89110835.9 (=ERA-350647)). However, there has been no report on the pharmaceutical effects of human BCDF on thrombocytopoiesis in order to cure platelet deficiency.

It has also been proposed to designate human BCDF as BSF-2 or interleukin 6 (IL-6) (*Nature*, 324, 73 (1986), EMBO. J., 6, 1219 (1987)). In this application, however, the term "BCDF" is used. Furthermore, human BCDF as used in this invention has no interferon activity and is thus different from IFN-$\beta_2$ having interferon activity (Published European patent application No. 0220574).

Platelets are one type of blood cells which play an important role in the hematostatic mechanism of living bodies. Platelets adhere and coagulate on damaged tissue and at the same time, release intracellular components which induce a series of coagulation reactions.

There are several different forms of thrombocytopenia all of which cause reduction in platelet count. One form is hereditary thrombocytopenia. Another is idiopathic thrombocytopenic purpura, while still another is aplastic anemia. A clinically more important form of thrombocytopenia is secondary thrombocytopenia which is induced by general irradiation with X-rays, or by the administration of drugs which prevent hematopoiesis, or by similar treatments.

In many cases, secondary thrombocytopenia is caused by chemotherapy, radiotherapy, bone marrow transplantation, or the like applied to cancer patients which results in inadequate formation of bone marrow megakaryocytes. Secondary thrombocytopenia is a dangerous disease which impedes the recovery of the patient and sometimes causes death by bleeding.

A therapy for thrombocytopenia which is currently most frequently used involves platelet transfusion in order to keep the platelet count at a value of more than 20,000/μl. However, in the case of bone marrow transplantation, for example, several months are required to increase the platelet count to the normal level so that transfusions of platelets inconsistent with HLA (human leukocyte antigen) are repeatedly required. As a result, anti-platelet antibody is formed and even after transfusion of platelets, the platelet count does not increase in many cases. In addition, there is also a danger of causing the likes of cytomegalovirus infection. Taking into account the fact that interstitial pneumonia is one of the three most frequent causes of postoperative death, it is preferred to keep the number of platelet transfusions as small as possible. Thrombocytopoiesis is the process in which megakaryocytic progenitor cells derived from multipotential stem cells are transformed into megakaryocytes via megakaryoblasts and platelets are then produced from megakaryocytes.

It is believed that this physiological thrombocytopoiesis would be controlled by humoral factors.

Therefore, if thrombocytopoiesis of the patient himself can be promoted by supplementing such humoral factors from an external source, bleeding would be prevented without transfusion of platelets. It can thus be expected that such administration of appropriate humoral factors would be effective for a radical treatment of thrombocytopenia.

Humoral factors which participate in thrombocytopoiesis, are thrombopoietin (TPO), megakaryocyte stimulating factor (MSF), thrombocytopoiesis stimulating factor (TSF), and the like. These factors would accentuate maturation and differentiation of megakaryocyte in vivo but the substances themselves are not yet elucidated ("IGAKU-NO-AYUMI" Progress in Medicine), 143, 528 (1987). On the other hand, it has been reported that megakaryocyte colony stimulating factor (Meg-CSF) and megakaryocyte colony potentiator (Meg-POT) are required for the formation of megakaryocyte colonies in vitro (Medical . Immunology, 14, 463 (1987)).

In recent years, it has been revealed as to Meg-CSF that IL 3, GM-CSF, EPO, and the like have Meg-CSF activity ("JIKKEN IGAKU" Experimental Medicine, 5, 822 (1987)). However, with respect to the other factors, their presence is merely suggested by various physiological activity assay systems.

The amino acid sequences, DNA sequences and other parameters of these factors are, of course, also unclear. Therefore, it has not yet been possible to industrially produce pure products appropriate to be used as drugs. More importantly, there has been no report to the effect that the administration of these factors, in vivo, would increase the count of platelets in peripheral blood. No factor has been found which stimulates thrombocytopoiesis and which promotes platelet production in the patient himself when administered to the patient.

SUMMARY OF THE INVENTION

Accordingly, one object of the present invention is to provide a composition for promoting thrombocytopoiesis in a patient suffering from thrombocytopenia, thus providing an agent for treating thrombocytopenia.

Briefly, this object and other objects of the present invention as hereinafter will become more readily apparent can be obtained in a method for treating thrombocytopenia by administering to a subject a composition containing a therapeutically effective amount of human BCDF or its biological equivalent.

DETAILED DESCRIPTION OF THE PREFERRED EMBODIMENTS

As a result of extensive investigation to solve the problem of effective treatment for thrombocytopenia, it has been found that (1) human BCDF can augment megakaryocytic colony formation in vitro synergistically with IL-3, or the like, and can induce maturation and differentiation of megakaryocytes by itself, and (2) in vivo administration of human BCDF can increase the platelet count in peripheral blood.

The present invention is the use of human B cell differentiation factor or its biological equivalent in the preparation of a composition for treating thrombocytopenia.

The human BCDF of the present invention has the following amino acid sequence (I) or (II) shown, for example, in Japanese Patent Aplication OPI Nos. 42688/88 and 56291/88 and Japanese Patent Application No. 289007/87.

amino acid insertion or amino acid addition, which derivatives have human BCDF activity.

That is, those equivalents which have a structure formed by adding one or a plurality of amino acids to human BCDF at the N-end and/or C-end thereof and those having a structure in which one or a plurality of amino acids in the human BCDF structure are replaced by other amino acids can also be used as the human BCDF of the present invention, as long as they have human BCDF activity. Preferably, human BCDF or human Ala-BCDF is used. The content of the human BCDF or its biological equivalent in accordance with the present invention is 0.0001 to 100 wt.%, preferably 0.1 to 1.0 wt.%, in a composition useful for treating thrombocytopenia.

Furthermore, the composition for treating thrombocytopenia of the present invention comprising human BCDF as the effective ingredient may also contain the usual stabilizer such as serum albumin, or the like and an excipient such as mannitol, or the like.

Furthermore, the composition for treating thrombocytopenia of the present invention may also contain, as

| AMino acid sequence (I): | | | | | | | | | | |
| --- | --- | --- | --- | --- | --- | --- | --- | --- | --- | --- |
| Pro | Val | Pro | Pro | Gly | Glu | Asp | Ser | Lys | Asp | Val |
| Ala | Ala | Pro | His | Arg | Gln | Pro | Leu | Thr | Ser | Ser |
| Glu | Arg | Ile | Asp | Lys | Gln | Ile | Arg | Tyr | Ile | Leu |
| Asp | Gly | Ile | Ser | Ala | Leu | Arg | Lys | Glu | Thr | Cys |
| Asn | Lys | Ser | Asn | Met | Cys | Glu | Ser | Ser | Lys | Glu |
| Ala | Leu | Ala | Glu | Asn | Asn | Leu | Asn | Leu | Pro | Lys |
| Met | Ala | Glu | Lys | Asp | Gly | Cys | Phe | Gln | Ser | Gly |
| Phe | Asn | Glu | Glu | Thr | Cys | Leu | Val | Lys | Ile | Ile |
| Thr | Gly | Leu | Leu | Glu | Phe | Glu | Val | Tyr | Leu | Glu |
| Tyr | Leu | Gln | Asn | Arg | Phe | Glu | Ser | Ser | Glu | Glu |
| Gln | Ala | Arg | Ala | Val | Gln | Met | Ser | Thr | Lys | Val |
| Leu | Ile | Gln | Phe | Leu | Gln | Lys | Lys | Ala | Lys | Asn |
| Leu | Asp | Ala | Ile | Thr | Thr | Pro | Asp | Pro | Thr | Thr |
| Asn | Ala | Ser | Leu | Leu | Thr | Lys | Leu | Gln | Ala | Gln |
| Asn | Gln | Trp | Leu | Gln | Asp | Met | Thr | Thr | His | Leu |
| Ile | Leu | Arg | Ser | Phe | Lys | Glu | Phe | Leu | Gln | Ser |
| Ser | Leu | Arg | Ala | Leu | Arg | Gln | Met | | | |
| or, | | | | | | | | | | |
| Amino acid sequence (II): | | | | | | | | | | |
| Ala | Pro | Val | Pro | Pro | Gly | Glu | Asp | Ser | Lys | Asp |
| Val | Ala | Ala | Pro | His | Arg | Gln | Pro | Leu | Thr | Ser |
| Ser | Glu | Arg | Ile | Asp | Lys | Gln | Ile | Arg | Tyr | Ile |
| Leu | Asp | Gly | Ile | Ser | Ala | Leu | Arg | Lys | Glu | Thr |
| Cys | Asn | Lys | Ser | Asn | Met | Cys | Glu | Ser | Ser | Lys |
| Glu | Ala | Leu | Ala | Glu | Asn | Asn | Leu | Asn | Leu | Pro |
| Lys | Met | Ala | Glu | Lys | Asp | Gly | Cys | Phe | Gln | Ser |
| Gly | Phe | Asn | Glu | Glu | Thr | Cys | Leu | Val | Lys | Ile |
| Ile | Thr | Gly | Leu | Leu | Glu | Phe | Glu | Val | Thr | Leu |
| Glu | Tyr | Leu | Gln | Asn | Arg | Phe | Glu | Ser | Ser | Glu |
| Glu | Gln | Ala | Arg | Ala | Val | Gln | Met | Ser | Thr | Lys |
| Val | Leu | Ile | Gln | Phe | Leu | Gln | Lys | Lys | Ala | Lys |
| Asn | Leu | Asp | Ala | Ile | Thr | Thr | Pro | Asp | Pro | Thr |
| Thr | Asn | Ala | Ser | Leu | Leu | Thr | Lys | Leu | Gln | Ala |
| Gln | Asn | Gln | Trp | Leu | Gln | Asp | Met | Thr | Thr | His |
| Leu | Ile | Leu | Arg | Ser | Phe | Lys | Glu | Phe | Leu | Gln |
| Ser | Ser | Leu | Arg | Ala | Leu | Arg | Gln | Met | | |

Amino acid sequence (I) is that of human BCDF and amino acid sequence (II) is a polypeptide having a structure obtained by adding one Ala to human BCDF at the N-end thereof (hereinafter referred to as human Ala-BCDF). However, the human BCDF of the present invention does not necessarily have the structure shown by either amino acid sequence (I) or (II) described above. In the present invention biological equivalents of h BCDF may be used which are derivatives of amino acid sequence (I) or amino acid sequence (II), obtainable by amino acid substitution, amino acid deletion, an auxiliary agent(s), one or more cytokines other than human BCDF, for example, IL-3, IL-1, IL-4, IL 5, G-CSF, GM-CSF, M-CSF, EPO and Meg-CSF, in addition to the human BCDF.

When such an auxiliary agent(s) is incorporated in the composition, the effects of the composition for treating thrombocytopenia can be increased synergistically. This is because IL-1, IL-3, IL-4, IL-5, G-CSF, GM-CSF, M-CSF, EPO and Meg-CSF can potentiate the promotion of hematopoietic functions. The amount of these auxiliary agents added to the composition is not particularly limited, but may be in a range of 0.0001 to 200000 wt.%, each, based on the human BCDF as 100%.

As already stated, the amount of these auxiliary agents added is not necessarily limited to the range described above, but may be appropriately determined depending upon conditions, the age of the patient, and other such factors.

The auxiliary agents such as IL-3, and the like need not always be administered as a drug together with human BCDF at the same time. That is, these auxiliary agents may be administered at an appropriate time prior to or after administration of the composition for treating thrombocytopenia containing human BCDF as the effective ingredient.

Of course, the composition for treating thrombocytopenia of the present invention may be used in combination with platelet transfusion therapy.

The composition for treating thrombocytopenia may be administered as an intravenous injection or as an intramuscular or subcutaneous injection. That is, the composition may be administered in any mode.

For preparing medical compositions of human BCDF, the methods described in Japanes Patent Application Nos. 289007/87 and 147594/88 can be applied.

The human BCDF used in the present invention may be any BCDF produced by human T cells, B cells, fibroblasts, etc. by known methods (Proc. Natl. Acad. Sci., USA, 82, 5490 (1985) or by culturing transformants obtained by transforming an appropriate host such as *E. coli*, yeast, monkey cells (COS cells), hamster cells, bacteria or the like by a recombinant DNA comprising a gene coding for human BCDF and a suitable vector. Furthermore, human BCDF purified from blood or urine samples or the like can also be used.

With respect to details of these production methods, reference is made to Japanese Patent Applications OPI Nos. 115024/86, 42688/88, 56291/88 and 157966/88.

The composition for treating thrombocytopenia produced in the present invention containing human BCDF as the effective ingredient accelerates maturation and differentiation of megakaryocytes and increases the platelet count in peripheral blood. Because of these activities, the composition is effective for treatment of patients suffering from thrombocytopenia, especially cancer patients undergoing chemotherapy, radiotherapy and bone marrow transplantation therapy, as well as patients with weak resistance to viral infection, and the like upon platelets transfusion, or the like.

Having generally described this invention, a further understanding can be obtained by reference to certain specific examples which are provided herein for purposes of illustration only and are not intended to be limiting unless otherwise specified.

EXAMPLE 1

Acceleration of megakaryocyte colony formation by human BCDF.

Bone marrow cells were prepared from the femurs of C57BL/6 mice in a conventional manner.

Among the bone marrow cells, $7.5 \times 10^4$ of non-adherent cells were cultured in 1 ml of Iskove's modification of Dulbecco's medium containing 1% bovine serum albumin, 360 μg/ ml of iron-saturated human transferrin, 0.98 μg/ ml of cholesterol, 100 U/ml of penicillin-streptomycin and 0.3% agar. The medium was supplemented with human BCDF of various concentrations as shown in Table 1 and 2.5% pokeweed mitogen stimulated murine spleen cells conditioned medium referred to as PWM-SCM; containing Meg-CSF activity).

After 7 days of culturing at 37° C., the agar discs were transferred to glass slides and fixed with 2% (v/v) glutaraldehyde.

Megakaryocyte colonies were counted after histochemical staining for acetylcholinesterase (AchE).

The results are shown in Table 1.

Furthermore, 20 U/ml of mouse IL-3 (manufactured by Genzyme Co., Ltd.) was supplemented in place of PWM-SCM. The results are shown in Table 2. In the case of human BCDF alone, the ability of forming megakaryocyte colonies was poor but human BCDF concentration-dependently induced the formation of megakaryocyte colonies in the copresence of PWM-SCM or mouse IL-3 having Meg-CSF activity.

A similar effect was noted also with human bone marrow cells. That is, compared to the addition of human IL-3 (100 U/ml) alone, the count of megakaryocyte colonies increased by 2.5 times by allowing human BCDF (100 ng/ml) to coexist with human IL-3 (100 U/ml).

TABLE 1

| Human BCDF (ng/ml) | PWM-SCM | Count of Megakaryocytic Colonies |
|---|---|---|
| 0 | (−) | 0 |
| 10 | (−) | 0 |
| 50 | (−) | 0 |
| 100 | (−) | 0 |
| 200 | (−) | 2 ± 1 |
| 0 | (+) | 3 ± 2 |
| 10 | (+) | 18 ± 1 |
| 50 | (+) | 29 ± 1 |
| 100 | (+) | 32 ± 1 |
| 200 | (+) | 37 ± 2 |

TABLE 2

| Human BCDF (ng/ml) | Mouse IL-3 | Count of Megakaryocytic Colonies |
|---|---|---|
| 0 | (+) | 2 ± 0 |
| 5 | (+) | 5 ± 0 |
| 10 | (+) | 7 ± 1 |
| 25 | (+) | 7 ± 1 |
| 50 | (+) | 11 ± 1 |
| 100 | (+) | 31 ± 4 |
| 200 | (+) | 32 ± 0 |

EXAMPLE 2

Promotion of maturation/differentiation of megakaryocytes by human BCDF.

Mouse bone marrow cells prepared by the method of Example 1 were inactivated by intrinsic cholinesterase and $1 \times 10^5$ of cells were cultured in 0.2 ml of serum-free liquid medium containing various concentrations of human BCDF.

After incubation at 37° C. for 4 days, the count of megakaryocytes in the bone marrow cells was determined by the count of cells positive to AchE which is an enzyme specific to mouse megakaryoycyte. Furthermore, the degree of maturation/differentiation was examined using, as indices, the diameters of magakaryocytes and the AchE activity. As shown in Tables 3 and 4, human BCDF concentration dependently increases the diameter of megakaryocytes and the AchE activity by itself.

Further in the single cell culture system where isolated single megakaryocytes were set up in 1 μl of liquid medium for one day, the diameter of megakaryocytes was significantly increased by the addition of 200 ng/ml of human BCDF, as shown in Table 5.

The foregoing results reveal that human BCDF directly acts on magakaryocytes to induce maturation/-differentiation of magakaryocytes.

Liquid culture, determination of AchE activity and single cell culture were carried out in accordance with the methods described in BLOOD, 67, 1512 (1986) and J. Clin. Invest., 79, 286 (1987).

TABLE 3

| Human BCDF (ng/ml) | Count of Megakaryocytes | Means Diameter (μm) |
| --- | --- | --- |
| 0 | 83.4 ± 4.8 | 20.4 ± 4.8 |
| 10 | 94.5 ± 14.4 | 25.4 ± 7.5 |
| 50 | 80.8 ± 10.3 | 29.8 ± 7.8 |
| 100 | 100.8 ± 18.8 | 32.7 ± 7.3 |
| 200 | 104.0 ± 18.9 | 34.1 ± 8.5 |

TABLE 4

| Human BCDF (ng/ml) | AchE Activity (AU) |
| --- | --- |
| 0 | 234 ± 52 |
| 1 | 262 ± 36 |
| 5 | 314 ± 42 |
| 10 | 328 ± 33 |
| 25 | 355 ± 44 |
| 50 | 352 ± 34 |
| 100 | 356 ± 24 |
| 200 | 430 ± 59 |

TABLE 5

| initial cell diameter (μm) | Rate of Cells Having Increased Diameter* (%) | |
| --- | --- | --- |
| | BCDF Not Added | BCDF Added (200 ng/ml) |
| 10–20 | 16 | 67 |
| 20–30 | 21 | 58 |
| >30 | 20 | 41 |

*Count of cells with increased diameter/count of total cells

EXAMPLE 3

Maturation of mouse bone marrow megakaryocytes by administration of human BCDF in vivo and increase of platelet count in peripheral blood.

Human BCDF, 5 to 10 μg, was disolved in 100 μl of 1% mouse serum containing PBS. The solution was intraperitoneally administered to 4 to 7 C57BL/6 mice (male, 6 to 7 weeks age) twice a day in 12 hour intervals for 5 days. As the control group, human BCDF inactivated by heat treatment at 100° C. for 40 minutes was similarly administered. Four hours after the final administration, the femurs were removed from the mice. The femurs were fixed with 10% formalin, dehydrated, embedded in plastic and longitudinally cut in sections and stained with hematoxylin-eosin to examine the effect of human BCDF on bone marrow megakaryocytes.

As shown by the results presented in Table 6, the number of megakaryocytes did not increase significantly in comparison to the control group, but the diameters of megakaryocytes significantly increased in the group administered human BCDF. This fact demonstrates BCDF-induced stimulation of megakaryocyte maturation of megakaryocytes.

TABLE 6

| Group | Megakaryocyte numbers | | Diameter of Megakaryocytes (μm) |
| --- | --- | --- | --- |
| | Counts (/mm²) | Corrected Counts | |
| 5 μg × 2 × 5 days (n = 7) | 96.31 ± 7.60 | 10.42 ± 0.88 | 25.99 ± 0.53* |
| Control (n-7) | 77.74 ± 4.96 | 9.91 ± 0.72 | 20.49 ± 0.67 |
| 10 μg × 2 × 5 days (n = 4) | 90.79 ± 5.63 | 9.58 ± 0.50 | 25.89 ± 0.51* |
| Control (n = 4) | 74.84 ± 7.48 | 9.74 ± 1.18 | 20.14 ± 0.73 |

*significant in p = 5%

In a similar manner, 0.5 to 10 μg of human BCDF was intraperitoneally administered to 4 to 8 mice for 5 days. Four hours after the final administration, blood was collected from the heart of the mice by a syringe treated with EDTA and the platelet count was measured with a blood autoanalyzer (manufactured by Coaltar Co., Ltd.). As shown in Table 7, the platelet count increased depending on the dose of human BCDF. Furthermore, as the experimental results show for blood collected with the passage of time the effect of human BCDF became most notable on day 4 after administration, as shown in Table 8.

TABLE 7

| Dose of Human BCDF | Count of Platelet ($\times 10^4/\mu l$) | |
| --- | --- | --- |
| | Control Group | BCDF-Administered Group |
| 0.5 μg × twice/day × 5 days | 107 ± 3 | 116 ± 6 |
| 1 μg × twice/day × 5 days | 102 ± 10 | 117 ± 11 |
| 2 μg × twice/day × 5 days | 104 ± 10 | 130 ± 17* |
| 5 μg × twice/day × 5 days | 102 ± 9 | 151 ± 13** |
| 10 μg × twice/day × 5 days | 101 ± 17 | 156 ± 3** |

*significant in p = 5%
**significant in p = 1%

TABLE 8

| Day After Administration | Count of Platelet ($\times 10^4/\mu l$) | |
| --- | --- | --- |
| | Control Group | BCDF-Administered Group |
| 1 | 100 ± 9 | 100 ± 10 |
| 2 | 102 ± 2 | 110 ± 9 |
| 3 | 101 ± 10 | 109 ± 18 |
| 4 | 98 ± 10 | 138 ± 15* |
| 5 | 102 ± 9 | 151 ± 13* |
| 6 | 102 ± 4 | 157 ± 16* |

*significant in p = 1%

EXAMPLE 4

Recovery of platelet count in peripheral blood of mice with thrombocytopenia by administration of human BCDF in vivo.

Human BCDF, 70 μg (10 μg/mouse/day×7 days) was continuously administered to five (5) DBA/2 mice (female, 8 week age) by an osmosis pump manufactured by Alza Co., Ltd. and implanted subcutaneously. Peripheral blood was collected from the hearts of the mice with passage of time and the platelet count in the blood was measured with an automatic hematological analyzer (Toa Medical Electronic Co., Ltd.). In comparison to the control group administered human albumin (80±6×10⁴/μl), the platelet count was 97±14×10⁴/μl in the group administered human BCDF for 7 days, showing a statistically significant increase.

Furthermore, when human BCDF inactivated by heat treatment at 100° C. for 40 minutes was administered, no significant increase of the platelet count was noted.

The effect of continuous perfusion with human BCDF was also noted in mice with thrombocytopenia induced by administration of a chemotherapeutic agent.

That is, in mice to which 150 mg/kg of 5-FU was intraveneously injected, the platelet count increased in the group subcutaneously administered human BCDF by an osmosis pump from 5 hours after administration of 5-FU, compared to the control group. This result is shown in Table 9.

Further in mice irradiated with 4.0 Gy X-ray, a significant acceleration of recovery of the platelet count was also noted in the group subcutaneously administered human BCDF by an osmosis pump after irradiation with X-rays, compared to the control group. This results are shown in Table 10.

Table 9

| Day After Administration of 5-FU | Count of Platelet ($\times 10^4/\mu l$) | |
|---|---|---|
| | Control Group | BCDF-Administered Group |
| Experiment (1) 7 | 10 ± 1 | 17 ± 10* |
| Experiment (2) 9 | 69 ± 9 | 146 ± 36* |
| Experiment (2) 12 | 221 ± 4 | 289 ± 8* |

*significant in p = 5%

TABLE 10

| Day After X Ray Irradiation | Count of Platelet ($\times 10^4/\mu l$) | |
|---|---|---|
| | Control Group | BCDF-Administered Group |
| 10 | 45 ± 10 | 63 ± 5* |
| 15 | 78 ± 9 | 106 ± 4* |

*significant in p = 5%

EXAMPLE 5

Increase of platelet count in peripheral blood in monkeys by administration of human BCDF in vivo.

Human BCDF was dissolved in 1% heat-inactivated autologous serum containing PBS. The solution was subcutaneously administered twice daily to cynomolgus monkeys (Macaca fascicularis, female, weighing 2.8 to 3.8 kg) in a dose of 2 ml each/time in 12 hour intervals every day for 14 consecutive days. Blood was collected from a vein of each animal and the blood cell count was measured with an automatic hematological analyzer (Toa Medical Electronic Co., Ltd.). As shown in Table 11, the platelet count increased with passage of time upon administration of human BCDF in doses of 5 μg/kg/day and 10 μg/kg/day (administered by dividing into two portions a day) and increased by 2 to 2.3 times at the maximum level prior to administration. The increase reverted to the original level prior to administration in about 2 weeks after administration. Also by administration in a dose of more than 20 to 80 μg/kg/day, the platelet count similarly increased by 2.2 to 2.5 times. The platelets derived from BCDF-administered monkey showed normal coagulation ability.

Furthermore, upon morphological examination of bone marrow, stimulation of bone marrow megakaryocytopoiesis was noted upon administration of human BCDF.

On the other hand, no increase of the leucocyte count was noted in a dose of 5 to 40 μg/kg/day, as shown in Table 11. For increasing the number of leucocytes such as granulocytes, and the like, administration in a dose greater than 80 μg/kg/day was required.

Furthermore, any increase in the erythrocyte count was not found in a dose of 5 to 500 μg/kg/day.

Such a specific platelet-increasing activity on the part of human BCDF was also recognized in the case of intravenous administration.

As stated above, it has been found that human BCDF exhibits the activity of increasing the platelet count of monkeys administered human BCDF in vivo.

TABLE 11

| | Dose of BCDF (μg/kg/day) | Prior to Administration | Count of Blood Cell In Peripheral Blood Day After Administration of BCDF | | | | | | | |
|---|---|---|---|---|---|---|---|---|---|---|
| | | | 2 | 4 | 7 | 10 | 14 | 16 | 20 | 28 |
| Platelet count (× 10⁴/μl) | 10 | 23 | 27 | 25 | 40 | 39 | 45 | 42 | 33 | 20 |
| | 5 | 19 | 14 | 17 | 41 | 44 | 38 | 40 | 27 | 20 |
| | 0 | 28 | 28 | 24 | 31 | 29 | 29 | 31 | 33 | 29 |
| Leucocyte count (× 10²/μl) | 10 | 79 | 107 | 108 | 85 | 92 | 92 | 88 | 92 | 77 |
| | 5 | 129 | 125 | 104 | 122 | 125 | 141 | 114 | 103 | 126 |
| | 0 | 78 | 66 | 46 | 77 | 74 | 76 | 78 | 83 | 85 |
| Erythrocyte count (× 10⁵/μl) | 10 | 62 | 57 | 52 | 53 | 49 | 56 | 55 | 63 | 62 |
| | 5 | 65 | 64 | 59 | 59 | 56 | 56 | 62 | 66 | 71 |
| | 0 | 62 | 62 | 59 | 62 | 62 | 63 | 61 | 66 | 61 |

Human BCDF was subcutaneously administered every day from Day 0 to Day 13 (divided into two portions a day).

What is claimed as new and desired to be secured by Letters Patent of the United States is:

1. A method for treating thrombocytopenia, comprising:

treating a subject suffering from thrombocytopenia with a composition containing a substance having human B cell differentiation activity.

2. The method of claim 1, wherein said substance having human B cell differentiation activity is human BCDF which has the amino acid sequence (I) as follows:

| Pro | Val | Pro | Pro | Gly | Glu | Asp | Ser | Lys | Asp | Val |
|---|---|---|---|---|---|---|---|---|---|---|
| Ala | Ala | Pro | His | Arg | Gln | Pro | Leu | Thr | Ser | Ser |
| Glu | Arg | Ile | Asp | Lys | Gln | Ile | Arg | Tyr | Ile | Leu |
| Asp | Gly | Ile | Ser | Ala | Leu | Arg | Lys | Glu | Thr | Cys |
| Asn | Lys | Ser | Asn | Met | Cys | Glu | Ser | Ser | Lys | Glu |

-continued

| Ala | Leu | Ala | Glu | Asn | Asn | Leu | Asn | Leu | Pro | Lys |
|---|---|---|---|---|---|---|---|---|---|---|
| Met | Ala | Glu | Lys | Asp | Gly | Cys | Phe | Gln | Ser | Gly |
| Phe | Asn | Glu | Glu | Thr | Cys | Leu | Val | Lys | Ile | Ile |
| Thr | Gly | Leu | Leu | Glu | Phe | Glu | Val | Tyr | Leu | Glu |
| Tyr | Leu | Gln | Asn | Arg | Phe | Glu | Ser | Ser | Glu | Glu |
| Gln | Ala | Arg | Ala | Val | Gln | Met | Ser | Thr | Lys | Val |
| Leu | Ile | Gln | Phe | Leu | Gln | Lys | Lys | Ala | Lys | Asn |
| Leu | Asp | Ala | Ile | Thr | Thr | Pro | Asp | Pro | Thr | Thr |
| Asn | Ala | Ser | Leu | Leu | Thr | Lys | Leu | Gln | Ala | Gln |
| Asn | Gln | Trp | Leu | Gln | Asp | Met | Thr | Thr | His | Leu |
| Ile | Leu | Arg | Ser | Phe | Lys | Glu | Phe | Leu | Gln | Ser |
| Ser | Leu | Arg | Ala | Leu | Arg | Gln | Met. | | | |

3. The method of claim 1, wherein said substance having human B cell differentiation activity is human BCDF which has the amino acid sequence (II) as follows:

| Ala | Pro | Val | Pro | Pro | Gly | Glu | Asp | Ser | Lys | Asp |
|---|---|---|---|---|---|---|---|---|---|---|
| Val | Ala | Ala | Pro | His | Arg | Gln | Pro | Leu | Thr | Ser |
| Ser | Glu | Arg | Ile | Asp | Lys | Gln | Ile | Arg | Tyr | Ile |
| Leu | Asp | Gly | Ile | Ser | Ala | Leu | Arg | Lys | Glu | Thr |
| Cys | Asn | Lys | Ser | Asn | Met | Cys | Glu | Ser | Ser | Lys |
| Glu | Ala | Leu | Ala | Glu | Asn | Asn | Leu | Asn | Leu | Pro |
| Lys | Met | Ala | Glu | Lys | Asp | Gly | Cys | Phe | Gln | Ser |
| Gly | Phe | Asn | Glu | Glu | Thr | Cys | Leu | Val | Lys | Ile |
| Ile | Thr | Gly | Leu | Leu | Glu | Phe | Glu | Val | Thr | Leu |
| Glu | Tyr | Leu | Gln | Asn | Arg | Phe | Glu | Ser | Ser | Glu |
| Glu | Gln | Ala | Arg | Ala | Val | Gln | Met | Ser | Thr | Lys |
| Val | Leu | Ile | Gln | Phe | Leu | Gln | Lys | Lys | Ala | Lys |
| Asn | Leu | Asp | Ala | Ile | Thr | Thr | Pro | Asp | Pro | Thr |
| Thr | Asn | Ala | Ser | Leu | Leu | Thr | Lys | Leu | Gln | Ala |
| Gln | Asn | Gln | Trp | Leu | Gln | Asp | Met | Thr | Thr | His |
| Leu | Ile | Leu | Arg | Ser | Phe | Lys | Glu | Phe | Leu | Gln |
| Ser | Ser | Leu | Arg | Ala | Leu | Arg | Gln | Met. | | |

4. The method of claim 1 or 2, wherein said substance having human B cell differentiation activity is human BCDF which has no sugar chain.

5. The method of claim 1, 2, or 3, wherein said substance having human B cell differentiation activity is human B cell differentiation factor which is produced in a prokaryote.

6. A method for treating thrombocytopenia, comprising:
treating a subject suffering from thrombocytopenia with a composition containing a substance having human B-cell differentiation activity as its principal active ingredient in combination with a pharmaceutically acceptable excipient.

7. A method for treating thrombocytopenia, comprising:
treating a subject suffering from thrombocytopenia with human B cell differentiation factor sugar chains attached thereto.

8. The method of claim 4, wherein said substance having human B cell differentiation activity is human B cell differentiation factor which is produced in prokaryote.

* * * * *

UNITED STATES PATENT AND TRADEMARK OFFICE
CERTIFICATE OF CORRECTION

PATENT NO. : 5,126,325

DATED : June 30, 1992

INVENTOR(S) : TADAMITSU KISHIMOTO ET AL

It is certified that error appears in the above-identified patent and that said Letters Patent is hereby corrected as shown below:

Col.   Line 4,    58,   after "IL" (fourth occurence) insert -- - --;

9,    23,   delete "This" and insert --These--;

Signed and Sealed this

Second Day of November, 1993

Attest:

BRUCE LEHMAN

Attesting Officer

Commissioner of Patents and Trademarks